US012539414B2

(12) United States Patent
Roelle et al.

(10) Patent No.: US 12,539,414 B2
(45) Date of Patent: Feb. 3, 2026

(54) SYSTEMS AND METHODS FOR BLOOD PUMP CONNECTORS

(71) Applicant: TC1 LLC, St. Paul, MN (US)

(72) Inventors: Dustin Roelle, Mountain House, CA (US); Dmitry Protsenko, Vallejo, CA (US); Mark Di Paola, Livermore, CA (US); Kathryn Smith-Petersen, Carlisle, MA (US); Emma DiasAbeygunawardena, Falcon Heights, MN (US)

(73) Assignee: TC1 LLC, St. Paul, MN (US)

( * ) Notice: Subject to any disclaimer, the term of this patent is extended or adjusted under 35 U.S.C. 154(b) by 1206 days.

(21) Appl. No.: 17/321,737

(22) Filed: May 17, 2021

(65) Prior Publication Data

US 2021/0361932 A1 Nov. 25, 2021

Related U.S. Application Data

(60) Provisional application No. 63/027,665, filed on May 20, 2020.

(51) Int. Cl.

| | |
|---|---|
| ***A61M 60/861*** | (2021.01) |
| ***A61M 60/178*** | (2021.01) |
| ***A61M 60/859*** | (2021.01) |

(52) U.S. Cl.

CPC ........ *A61M 60/861* (2021.01); *A61M 60/178* (2021.01); *A61M 60/859* (2021.01)

(58) Field of Classification Search

CPC .............. A61M 60/861; A61M 60/178; A61M 60/859; A61M 2205/502; A61M 60/878; A61M 60/216; A61M 60/88; A61M 39/00; A61M 39/10; A61M 2039/1033; H01R 2201/12; H01R 13/623; H01R 13/625

See application file for complete search history.

(56) References Cited

U.S. PATENT DOCUMENTS

| | | | | |
|---|---|---|---|---|
| 9,042,979 | B2 | 5/2015 | Peters et al. | |
| 10,608,386 | B2 | 3/2020 | Lehnert et al. | |
| 2013/0225909 | A1* | 8/2013 | Dormanen .......... | A61M 60/178 600/16 |
| 2015/0222050 | A1* | 8/2015 | Behning ............ | H01R 13/6456 439/314 |
| 2019/0334283 | A1 | 10/2019 | Di Paola et al. | |
| 2021/0113105 | A1 | 4/2021 | Wei | |
| 2021/0113126 | A1 | 4/2021 | Donnay et al. | |

* cited by examiner

*Primary Examiner* — Jerrah Edwards
*Assistant Examiner* — Jose H. Trevino, III
(74) *Attorney, Agent, or Firm* — Armstrong Teasdale LLP

(57) ABSTRACT

Systems and methods for connections in a medical device system are provided. A connector system includes a connector receptacle including first electrical contacts, a connector insert including second electrical contacts and at least one pin, and a locking member rotatably coupled to the connector receptacle, the locking member including a housing and a guide member, the guide member including an annular body that defines at least one groove including a first locking detent and a second locking detent, the at least one pin operable to traverse the at least one groove, engage the first locking detent in a first locked configuration, and engage the second locking detent in a second locked configuration when the connector insert is inserted into the connector receptacle.

20 Claims, 8 Drawing Sheets

SYSTEMS AND METHODS FOR BLOOD PUMP CONNECTORS

CROSS-REFERENCE TO RELATED APPLICATIONS

This application claims priority to U.S. provisional application Ser. No. 63/027,665, filed May 20, 2020, which is incorporated herein by reference in its entirety.

FIELD OF THE DISCLOSURE

This disclosure relates to implantable medical devices, and more particularly, this disclosure relates to connection systems for use in implantable blood pumps.

BACKGROUND

Ventricular assist systems (VASs) may include ventricular assist devices (VADs), such as implantable blood pumps used for both short-term (i.e., days, months) and long-term (i.e., years or a lifetime) applications where a patient's heart is incapable of providing adequate circulation, commonly referred to as heart failure or congestive heart failure. A patient suffering from heart failure may use a VAS while awaiting a heart transplant or as a long-term destination therapy. In another example, a patient may use a VAS while recovering from heart surgery. Thus, a VAS can supplement a weak heart (i.e., partial support) or can effectively replace the natural heart's function. VASs can be implanted in the patient's body and powered by an electrical power source inside or outside the patient's body.

According to the American Heart Association, more than five million Americans are living with heart failure, with about 670,000 new cases diagnosed every year. People with heart failure often have shortness of breath and fatigue. Years of living with blocked arteries or high blood pressure can leave your heart too weak to pump enough blood to your body. As symptoms worsen, advanced heart failure develops.

Operation of a VAD can be controlled and/or affected by a controller communicatively coupled with the VAD. The controller can be an external controller or an implanted controller. The operation of the controller can be important to the operation of the VAD and can control all or portions of the operation of the VAD including, for example, a speed of the VAD. Some controllers, for example, can monitor one or several parameters relevant to the patient and can affect operation of the VAD according to those one or several monitored parameters. This can include, for example, changing the VAD speed in response to an increase or decrease in physical activity, or the like. Controllers are typically connected to the VAD via a wired connection. Additionally, some controllers are connected to one or more power sources via a wired connection. The connectors in these wired connections may be improved to facilitate ease of use and to improve durability. Accordingly, new systems, methods, and/or connectors are desired.

BRIEF SUMMARY OF THE DISCLOSURE

In one embodiment, the present disclosure is directed to a connector system for a medical device system. The connector system includes a connector receptacle including first electrical contacts, a connector insert including second electrical contacts and at least one pin, and a locking member rotatably coupled to the connector receptacle, the locking member including a housing and a guide member, the guide member including an annular body that defines at least one groove including a first locking detent and a second locking detent, the at least one pin operable to traverse the at least one groove, engage the first locking detent in a first locked configuration, and engage the second locking detent in a second locked configuration when the connector insert is inserted into the connector receptacle.

In another embodiment, the present disclosure is directed to a medical device system. The medical device system includes an implantable medical device, a controller, and a driveline coupling the implantable medical device to the controller, the driveline including a connector system that includes a connector receptacle comprising first electrical contacts, a connector insert including second electrical contacts and at least one pin, and a locking member rotatably coupled to the connector receptacle, the locking member including a housing and a guide member, the guide member including an annular body that defines at least one groove including a first locking detent and a second locking detent, the at least one pin operable to traverse the at least one groove, engage the first locking detent in a first locked configuration, and engage the second locking detent in a second locked configuration when the connector insert is inserted into the connector receptacle.

In yet another embodiment, the present disclosure is directed to a method of assembling a connector system for use in a medical device system. The method includes coupling a connector receptacle to an end of a first piece of a driveline, the connector receptacle including first electrical contacts, coupling a connector insert to an end of a second piece of the driveline, the connector insert including second electrical contacts and at least one pin, and rotatably coupling a locking member to the connector receptacle, the locking member including a housing and a guide member, the guide member including an annular body that defines at least one groove including a first locking detent and a second locking detent, the at least one pin operable to traverse the at least one groove, engage the first locking detent in a first locked configuration, and engage the second locking detent in a second locked configuration when the connector insert is inserted into the connector receptacle.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

Figure 1:
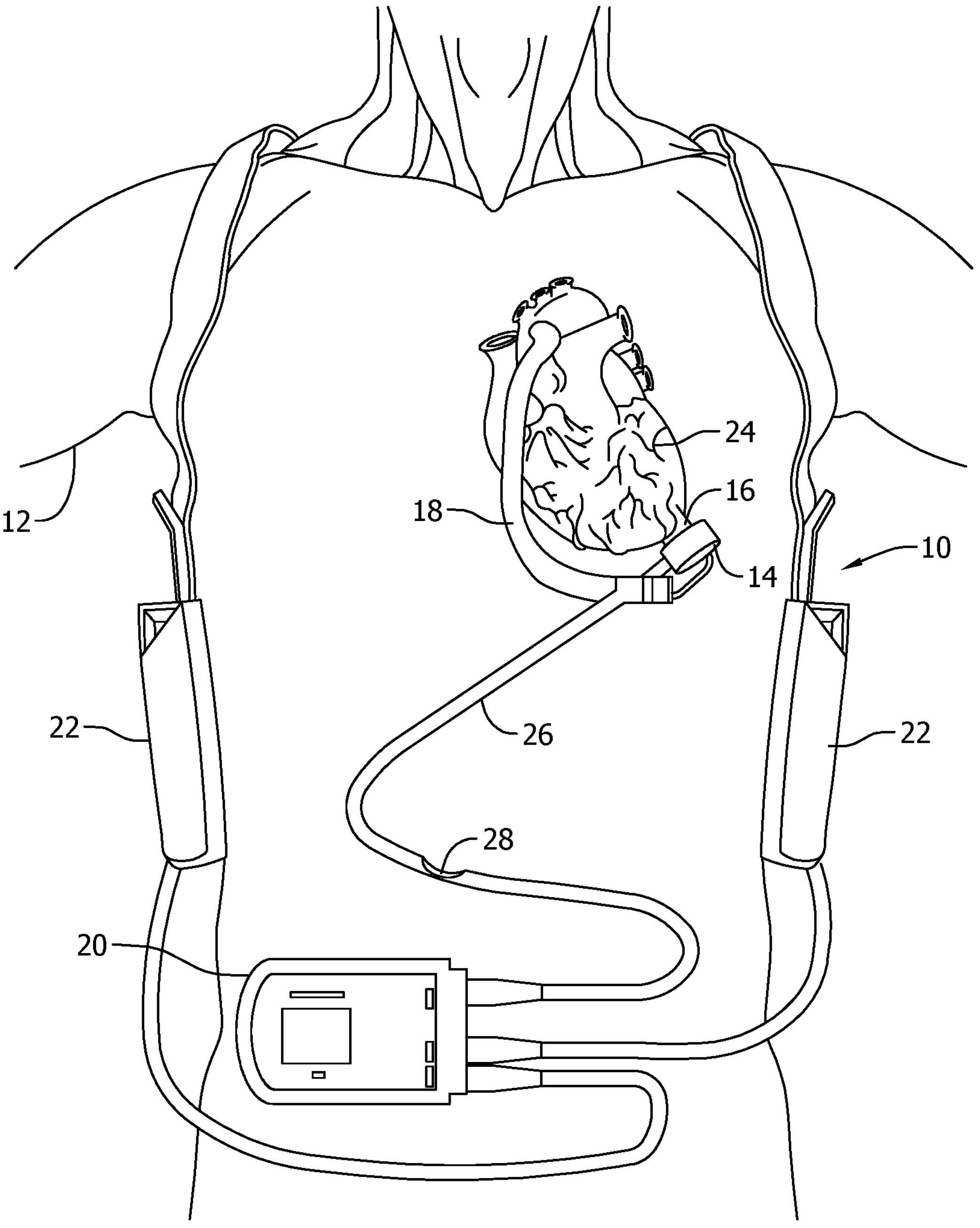
FIG. 1 is a schematic diagram of one embodiment of a mechanical circulatory support system.

The disclosure provides systems and methods for connections in a medical device system. A connector system includes a connector receptacle including first electrical contacts, a connector insert including second electrical contacts and at least one pin, and a locking member rotatably coupled to the connector receptacle. The locking member includes a housing and a guide member, the guide member including an annular body that defines at least one groove including a first locking detent and a second locking detent. The at least one pin is operable to traverse the at least one groove, engage the first locking detent in a first locked configuration, and engage the second locking detent in a second locked configuration when the connector insert is inserted into the connector receptacle.

This application is related to U.S. patent application Ser. No. 16/395,134, filed Apr. 25, 2019, which is incorporated by reference herein in its entirety.

Circulatory support systems are increasingly used to support blood circulation in patients. These circulatory systems can include an implantable blood pump such as a VAD and a controller. In some embodiments, the controller can directly control the implantable blood pump via one or several control signals, and/or the controller can provide one or several parameters that can be used by the implantable blood pump to affect operation of the implantable blood pump, such as, for example, to change a speed of the implantable blood pump.

Due to this role of the controller in affecting operation of the implantable blood pump, reliability and ruggedness of the controller are important. However, in many instances, controllers are coupled to either a power source such as an external power source or to the implantable blood pump via one or several cables, wires, drivelines, or the like. The connection of the controller with the other components relies on connectors that form this coupling. While numerous improvements have been made to connectors to minimize risk of damage to the connectors and to improve connector reliability, further improvements are desired.

Such improvements to the connectors may enhance the connector to minimize susceptibility to environmental factors, corrosion, and/or contamination of all or portions of the connector with foreign objects that may hinder coupling. Such improvements may further facilitate connecting the connector and may facilitate aligning the connector insert and the connector receptacle to improve connection. In some embodiments, for example, a connector may include one or several seals that seal contacts and/or that isolate contacts. In some embodiments, the connector can include one or several features that can facilitate draining of the connector of any fluid that may be in the connector at the time of coupling. In some embodiments, the connector can include one or several features that automatically align the connector when coupled and/or that facilitate coupling of the connector.

These features that facilitate alignment can include, for example, the shape of the connector insert and/or the connector receptacle. In some embodiments, for example, the connector insert has a particular shape, and the connector receptacle has a complementary shape that allows insertion of the connector insert in one of a finite number of orientations into the connector receptacle. In some embodiments, the shape can allow insertion of the connector insert into the connector receptacle in multiple orientations (e.g., in two orientations oriented 180° relative to each other). In some embodiments, the contacts in the connector receptacle and the contacts of the connector insert can be arranged to properly mate when the connector insert is inserted into the connector receptacle in any of the finite number of orientations.

Referring now to the drawings wherein like reference numerals are used to identify identical components in the various views, FIG. 1 illustrates one exemplary embodiment of a mechanical circulatory support system 10, also referred to herein as an implantable blood pump system 10. Mechanical circulatory support system 10 is partially implanted in a patient's body 12. Mechanical circulatory support system 10 includes an implantable blood pump 14, a ventricular cuff 16, an outflow cannula 18, a system controller 20, and external power sources 22.

Implantable blood pump 14 may include a VAD that is attached to an apex of the left ventricle, as illustrated, or the right ventricle, or both ventricles of the heart 24. The VAD may include a centrifugal (as shown) or axial flow pump that is capable of pumping the entire output delivered to the left ventricle from the pulmonary circulation (i.e., up to 10 liters per minute). Related blood pumps applicable to the present disclosure are described in greater detail below and in U.S. Pat. Nos. 5,695,471, 6,071,093, 6,116,862, 6,186,665, 6,234,772, 6,264,635, 6,688,861, 7,699,586, 7,976,271, 7,997,854, 8,007,254, 8,152,493, 8,652,024, and 8,668,473 and U.S. Patent Publication Nos. 2007/0078293, 2008/0021394, 2009/0203957, 2012/0046514, 2012/0095281, 2013/0096364, 2013/0170970, 2013/0121821, and 2013/0225909, all of which are incorporated herein by reference for all purposes in their entirety.

Blood pump 14 may be attached to heart 24 via ventricular cuff 16, which is sewn to heart 24 and coupled to blood pump 14. The other end of blood pump 14 connects to the ascending aorta via outflow cannula 18 so that the VAD effectively diverts blood from the weakened ventricle and propels it to the aorta for circulation to the rest of the patient's vascular system.

In FIG. 1, mechanical circulatory support system 10 is illustrated in a configuration in which powered operation is enabled via external power source 22. A driveline 26 which exits through the patient's abdomen 28, connects implanted blood pump 14 to system controller 20, which monitors operation of system 10. Related controller systems applicable to the present disclosure are described in greater detail below and in U.S. Pat. Nos. 5,888,242, 6,991,595, 8,323,174, 8,449,444, 8,506,471, 8,597,350, and 8,657,733 and U.S. Patent Publication Nos. 2005/0071001 and 2013/0314047, all of which are incorporated herein by reference for all purposes in their entirety.

The system may be powered by one, two, or more external power sources 22. In some embodiments, one or several energy storage components, such as, for example, one or several batteries, in controller 20 can power the mechanical circulatory support system 10. It will be appreciated that although system controller 20 and power source 22 are illustrated outside/external to the patient body, driveline 26, system controller 20 and/or power source 22 may be partially or fully implantable within the patient, as separate components or integrated with blood bump 14. In some embodiments, for example, system controller 20 can be implanted within the patient's body, and can receive power from power source 22 that is external to the patient's body. In some embodiments, this power can be provided to controller 20 via a wired or wireless connection between controller 20 and power source 22. In some embodiments, this wireless connection can include a transcutaneous energy transfer system (TETS) that can, for example, include one or several resonant circuits. Examples of such modifications are further described in U.S. Pat. No. 8,562,508 and U.S. Patent Publication No. 2013/0127253, all of which are incorporated herein by reference for all purposes in their entirety.

Figure 2:
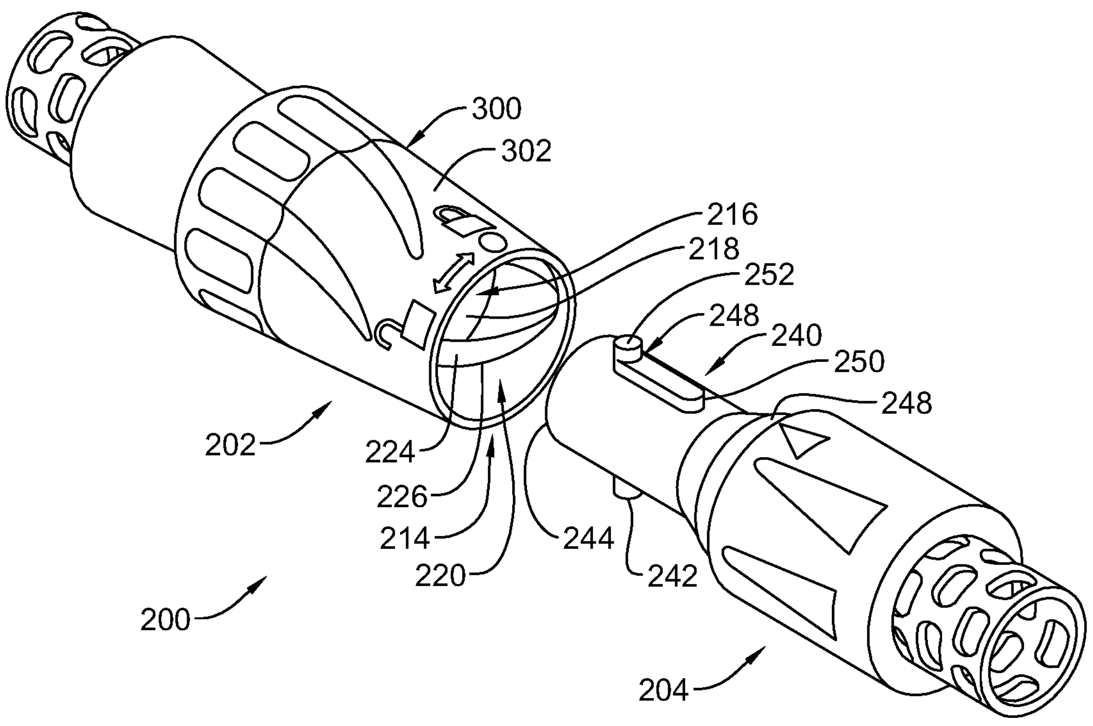
FIG. 2 is a perspective view of one embodiment of a connector system that may be used with the mechanical circulatory support system shown in FIG. 1.

FIG. 2 is a perspective view of one exemplary embodiment of a connector system 200 that may be used with mechanical circulatory support system 10.

Connector system 200 includes a connector receptacle 202 and a connector insert 204. One or both of connector receptacle 202 and connector insert 204 may be located on or in a medical device such as, for example, in or on a component of mechanical circulatory support system 10 including, for example, implantable blood pump 14, system controller 20, one or both of the external power sources 22, and/or driveline 26. In the embodiment shown in FIG. 2, connector receptacle 202 and connector insert 204 are located in driveline 26, and driveline 26 is a two-piece driveline 26. Specifically, the connector receptacle 202 is located at an end of a first piece of driveline 26 (i.e., at an end of a first cable) and connector insert 204 is located at an end of a second piece of driveline 26 (i.e., at an end of a second cable). In some embodiments, system controller 20 is coupled to implantable blood pump 14 via driveline 26, and connector system 200 connects the first and second pieces of driveline 26.

Connector receptacle 202 includes a top 214, also referred to herein as an end 214, a recessed bottom 216, and a side 218, also referred to herein as a wall 218 or as a sidewall 218 that connects top 214 and bottom 216. In some embodiments, sidewall 218 can extend from top 214 to bottom 216 of connector receptacle 202. Connector receptacle 202, and specifically wall 218 and bottom 216 of connector receptacle 202 define a receptacle volume 220 that can be accessed via an opening defined by top 214 of connector receptacle 202.

Although described herein as being located at an end of a piece of driveline 26, connector receptacle 202 can alternatively be located at an end of a tether containing, for example, one or more wires, one or more light guides, or the like. The tether may include driveline 26, a cable connecting an extra power source 22 to controller 20, or the like.

In one embodiment, connector receptacle 202 includes a plurality of contacts (not shown in FIG. 2). In some embodiments, the contacts include a plurality of pins which can be arranged in any desired layout (e.g., a circle or ring). The contacts are configured for mating with corresponding contacts of connector insert 204 when connector insert 204 is coupled with connector receptacle 202. In some embodiments, the contacts are located at or on bottom 216 of connector receptacle 202.

In this embodiment, connector receptacle 202 includes at least one mating feature 224 that engages orientation features of connector insert 204 to transition connector insert 204 to a desired orientation, and/or alignment with respect to connector receptacle 202. In some embodiments, mating feature 224 engages the orientation features of connector insert 204 to transition connector insert 204 to the desired orientation and/or alignment with respect to connector receptacle 202 when or while connector insert 204 is inserted into connector receptacle 202. In some embodiments, for example, mating feature 224 may interact with the orientation features of connector insert 204 such that the further connector insert 204 is inserted into connector receptacle 202, the closer the actual alignment, and/or orientation of connector insert 204 is to the desired orientation, and/or alignment.

Mating feature 224 may include one or more cam surfaces 226 (shown best in FIGS. 5A, 5B, 6A, 6B, 7A, and 7B) configured to engage the orientation feature, which can be a following surface, to bias connector insert 204 to a desired alignment with respect to connector receptacle 202 when connector insert 204 is inserted into connector receptacle 202. Specifically, in some embodiments, the following surface of connector insert 204 can slide along or across all or portions of cam surfaces 226. Cam surfaces 226 can extend and/or wrap around all or portions of connector receptacle 202, and specifically around all or portions of end 214.

In one embodiment, cam surfaces 226 cause connector insert 204 to rotate with respect to connector receptacle 202 when connector insert 204 is inserted into connector receptacle 202. In some embodiments, cam surfaces 226 are sized, shaped, and/or positioned such that rotation of connector insert 204 with respect to connector receptacle 202 stops before any of the plurality of contacts mates with, engages with, and/or contacts any of the contacts of connector insert 204.

Connector insert 204 includes a body 240 having sides 242, also referred to as exterior sides 242, and a front 244. Body 240 of connector insert 204 can be sealed, and specifically can be hermetically sealed. Connector insert 204 includes insert contacts (not shown in FIG. 2) which may be arranged in any desired layout (e.g., arranged in a circle or ring).

As shown in FIG. 2, connector insert 204 also includes an annular indicator line 246. Indicator line 246 enables a user to determine whether connector insert 204 is properly coupled to connector receptacle 202, as described herein.

In one embodiment, connector insert 204 includes an orientation feature 248, also referred to herein as a following feature 248 or following surface 248, configured to engage with mating feature 224 of the connector receptacle 202 to rotate connector insert 204 to a desired alignment with respect to connector receptacle 202 while connector insert 204 is inserted into connector receptacle 202. In some embodiments, following surface 248 extends from side 242 of body 240 of connector insert 204, and in some embodiments, following surface 248 can extend radially outwardly from side 242 of body 240 of connector insert 204.

Following surface 248 includes a key 250 and a pin 252 in the embodiment shown in FIG. 2. Pin 252 is configured to engage with cam surfaces 226 of mating feature 224, and specifically, is configured to slide along and/or across cam surface 226. In some embodiments, following surface 248 includes two following surfaces 248 arranged opposite one another on body 240. This allows connector insert 204 to be insertable into connector receptacle at two different orientations (180° offset from each other).

Figure 3:
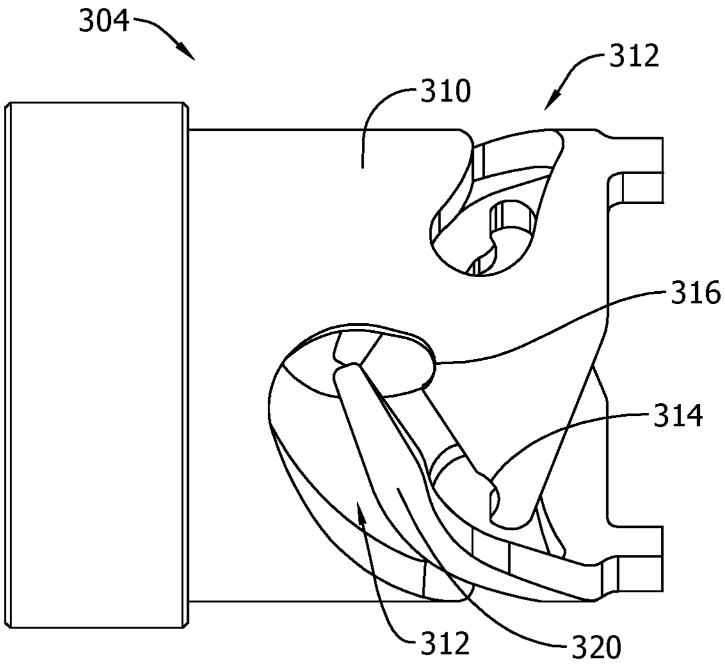
FIG. 3 is a side view of one embodiment of a guide member that may be used with the connector system shown in FIG. 2.
Figure 4:
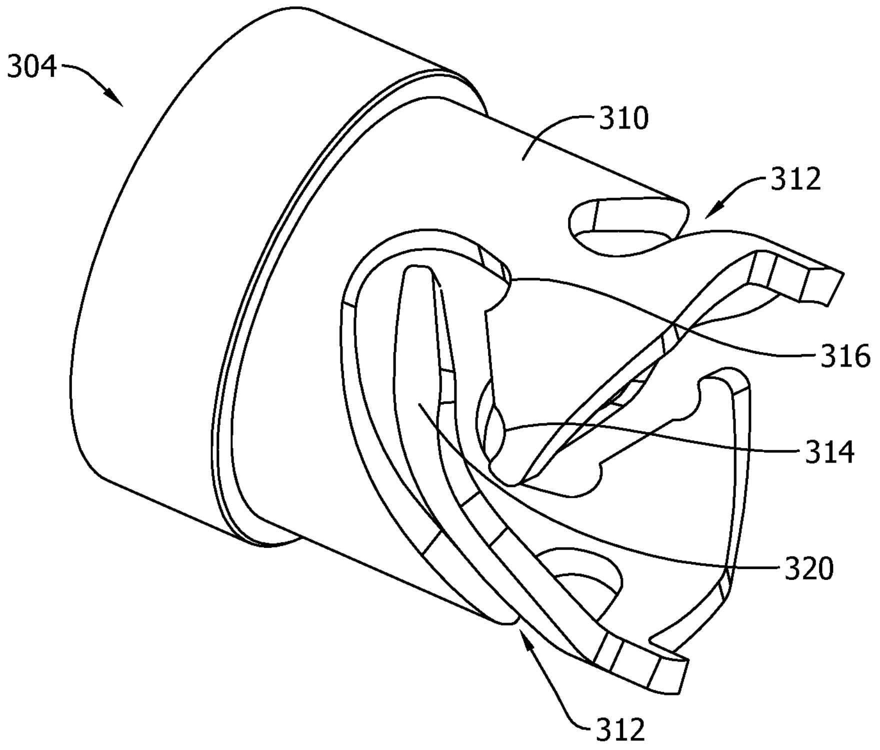
FIG. 4 is a perspective view of the guide member shown in FIG. 3.

Connector system 200 further includes a locking member 300 that includes a housing 302 and a guide member 304 (not shown in FIG. 2). Guide member 304 is positioned within housing 302. FIG. 3 is a side view of an exemplary embodiment of guide member 304, and FIG. 4 is a perspective view of guide member 304. Housing 302 of locking member 300 extends at least partially around connector receptacle 202, and specifically, locking member 300 can include a channel in which connector receptacle 202 is at least partially received such locking member 300 extends around at least a portion of connector receptacle 202. In this embodiment, locking member 300 is rotatable about connector receptacle 202.

As described in detail herein, locking member 300, and specifically, guide member 304 engages with connector insert 204 to retain coupling between connector receptacle 202 and connector insert 204. In one embodiment, guide member 304 engages pins 252 to retain coupling between connector receptacle 202 and connector insert 204.

As shown in FIGS. 3 and 4, guide member 304 includes an annular body 310 that defines two grooves 312 (corresponding to the two pins 252 on connector insert 204). Each groove 312 is generally u-shaped, and includes a plurality of locking detents. Specifically, in the embodiment shown, each groove 312 includes a first locking detent 314 and a second locking detent 316.

As described below, the engagement between pin 252 and groove 312 improves the locking safety of connector system 200 by preventing accidental disconnections, and making it more evident to a user when connector insert 204 fully engages connector receptacle 202.

In one embodiment, guide member 304 includes a spring 320 that at least partially defines groove 312. Spring 320 is a flexible projection that is biased towards first and second locking detents 314 and 316. Accordingly, when pin 252 traverses groove 312, spring 320 urges pin 252 towards first and second locking detents 314 and 316.

Figure 5A:
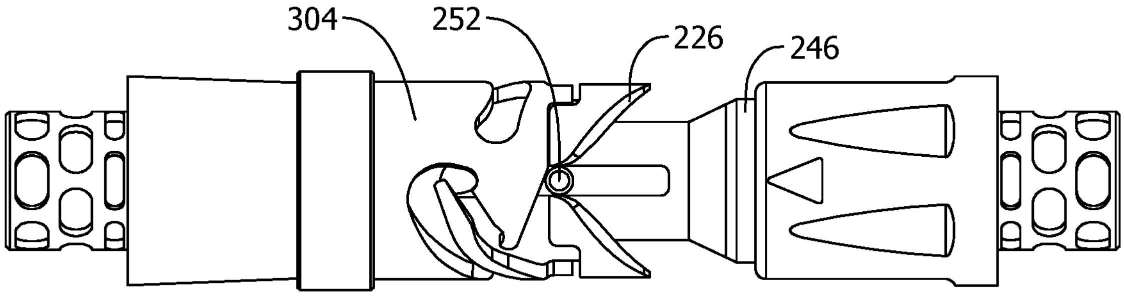
FIGS. 5A-5C illustrate initial insertion of a connector insert into a connector receptacle in the connector system shown in FIG. 2.
Figure 5B:
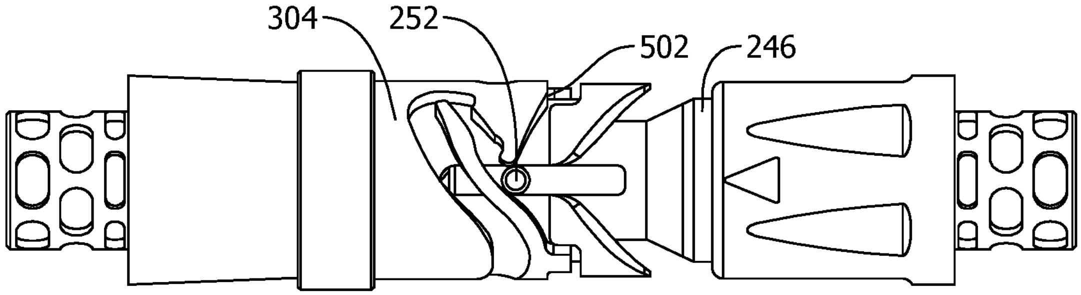
Figure 5C:
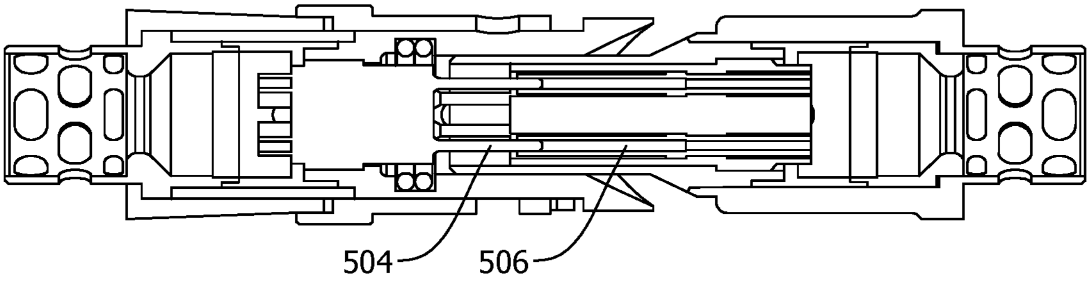

FIGS. 5A-5C illustrate initial insertion of connector insert 204 into connector receptacle 202. Specifically, FIGS. 5A and 5B are side views of connector system 200, and FIG. 5C is a side cross-sectional view of connector system 200 at the position shown in FIG. 5B. For clarity, housing 302 is omitted in FIGS. 5A-5C.

As shown in FIG. 5A, as connector insert 204 is initially inserted into connector receptacle 202, pin 252 contacts cam surfaces 226 and slides along cam surfaces 226 until pin 252 contacts guide member 304. Once pin 252 contacts guide member 304, a front guide surface 502 of guide member 304 guides pin 252 into groove 312, as shown in FIG. 5B. Specifically, an axial force applied by connector insert 204 causes guide member 304 to rotate relative to connector receptacle 202 (and connector insert 204), guiding pin 252 into groove 312. At this point, as shown in FIG. 5C, electrical contact is established between first contacts 504 in connector receptacle 202 and second contacts 506 in connector insert 204. During the initial insertion shown in FIGS. 5A and 5B, indicator line 246 is visible from an exterior of connector system 200.

Figure 6A:
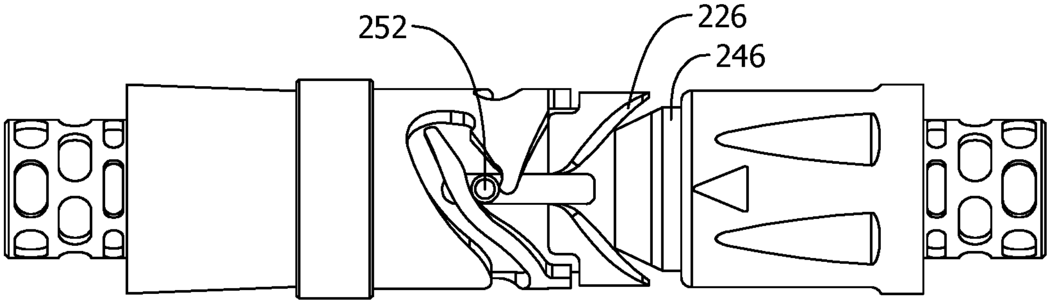
FIGS. 6A-6C illustrate continued insertion of the connector insert into the connector receptacle.
Figure 6B:
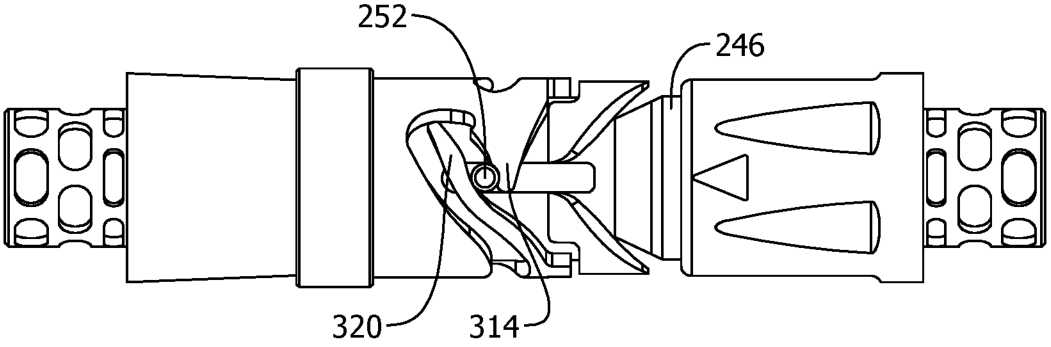
Figure 6C:
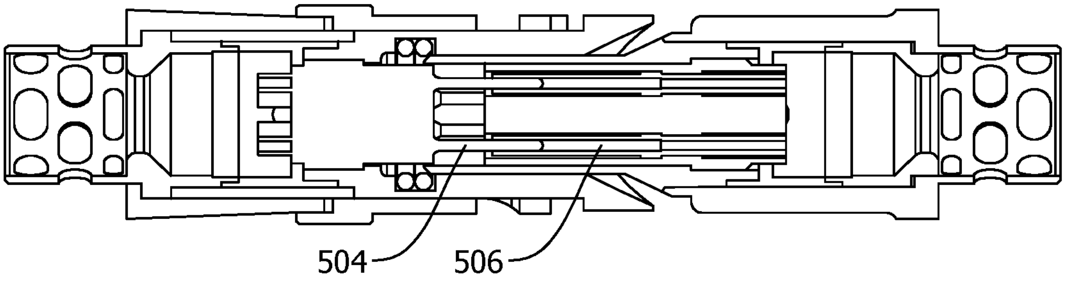

FIGS. 6A-6C illustrate continued insertion of connector insert 204 into connector receptacle 202. Specifically, FIGS. 6A and 6B are side views of connector system 200, and FIG. 6C is a side cross-sectional view of connector system 200 at the position shown in FIG. 6B. For clarity, housing 302 is omitted in FIGS. 6A-6C.

As shown in FIG. 6A, as pin 252 traverses groove 312, the axial force applied by pin 252 causes spring 320 to initially flex in the same direction as the axial force and causes guide member 304 to further rotate. However, the biasing of spring 320 counteracts this flexing and urges pin 252 into first locking detent 314, putting connector system 200 in a first locked configuration, as shown in FIG. 6B. This partially secures connector insert 204 to connector receptacle 202, and electrical contact is maintained between first contacts 504 and second contacts 506, as shown in FIG. 6C. However, indicator line 246 is still visible from the exterior of connector system 200.

Figure 7A:
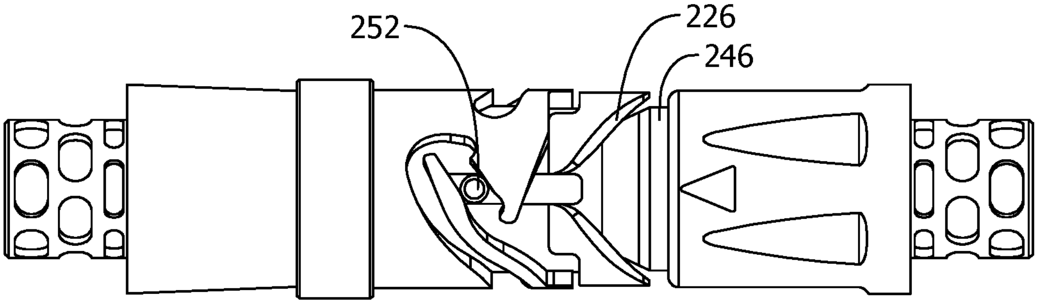
FIGS. 7A-7C illustrate final insertion of the connector insert into the connector receptacle.
Figure 7B:
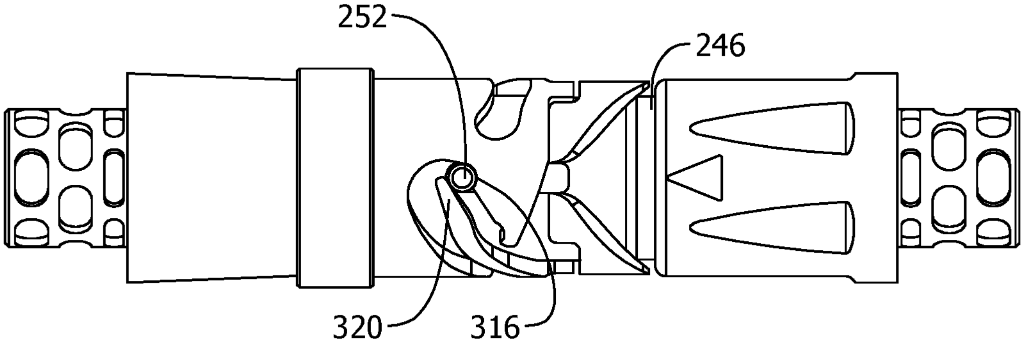
Figure 7C:
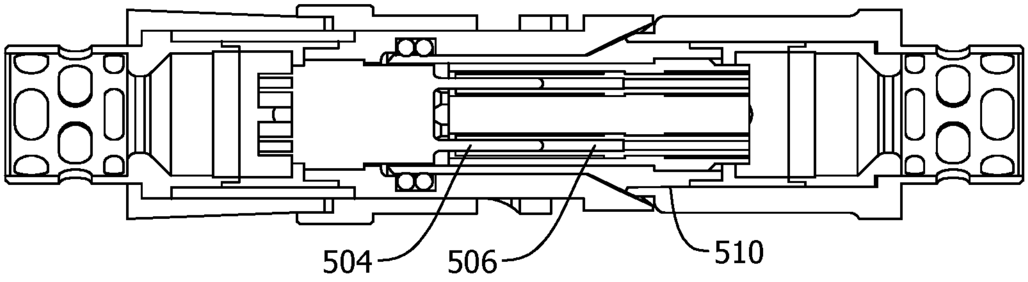

FIGS. 7A-7C illustrate final insertion of connector insert 204 into connector receptacle 202. Specifically, FIGS. 7A and 7B are side views of connector system 200, and FIG. 7C is a side cross-sectional view of connector system 200 at the position shown in FIG. 7B. For clarity, housing 302 is omitted in FIGS. 7A-7C.

As shown in FIG. 7A, once pin 252 engages first locking detent 314, the user can apply additional force (e.g., a combination of torque and axial force) to transition pin 252 from first locking detent 314 to second locking detent 316 along groove 312. Specifically, the additional force flexes spring 320, allowing pin 252 to further traverse groove 312. The biasing of spring 320 then urges pin 252 into second locking detent 316, putting connector system 200 in a second locked configuration, as shown in FIG. 7B. This fully secures connector insert 204 to connector receptacle 202, and electrical contact is maintained between first contacts 504 and second contacts 506, as shown in FIG. 7C. In addition, physical contact between a shoulder 510 of connector insert 204 and cam surfaces 226 provides a seal for connector system 200, preventing solids or liquids from seeping into connector system 200 and interfering with the electrical contact. In the locked configuration, indicator line 246 is not visible from the exterior of connector system 200.

FIGS. 8A-8D are side views of connector system 200 illustrating various stages of insertion of connector insert 204 into connector receptacle 202. As shown in FIGS. 8A-8D, connector insert 204 and housing 302 include various indicators to enable the user to quickly and easily determine the status of the connection between connector insert 204 and connector receptacle 202. Specifically, in this embodiment, connector insert 204 includes an arrow indicator 802. Further, housing 302 includes an unlock indicator 804, a lock indicator 806, and a transition indicator 808 extending between unlock indicator 804 and lock indicator 806.

Figure 8A:
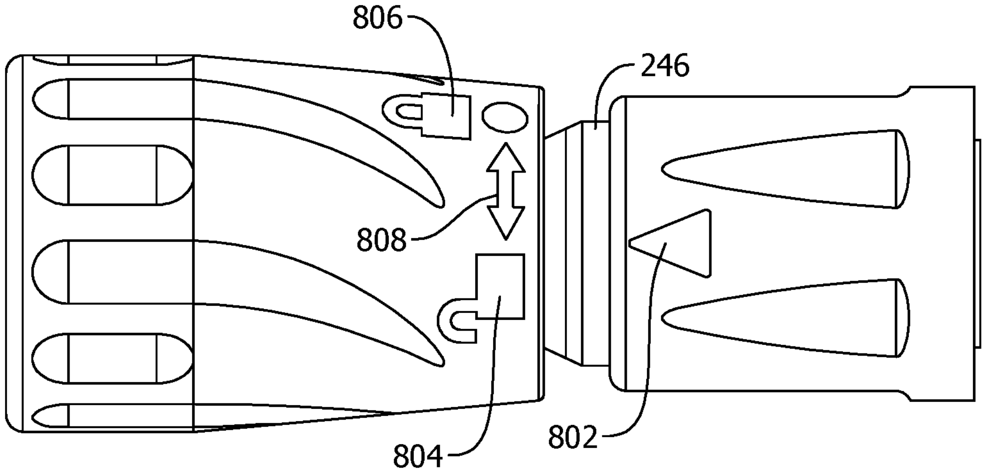
FIGS. 8A-8D are side views of the connector system illustrating various stages of insertion of the connector insert into the connector receptacle.

FIG. 8A shows connector insert 204 and housing 302 during initial insertion (i.e., prior to pin 252 engaging first locking detent 314). In this configuration, indicator line 246 is visible. Further, arrow indicator 802 on connector insert 204 is generally aligned with a first end of transition indicator 808 proximate unlock indicator 804.

Figure 8B:
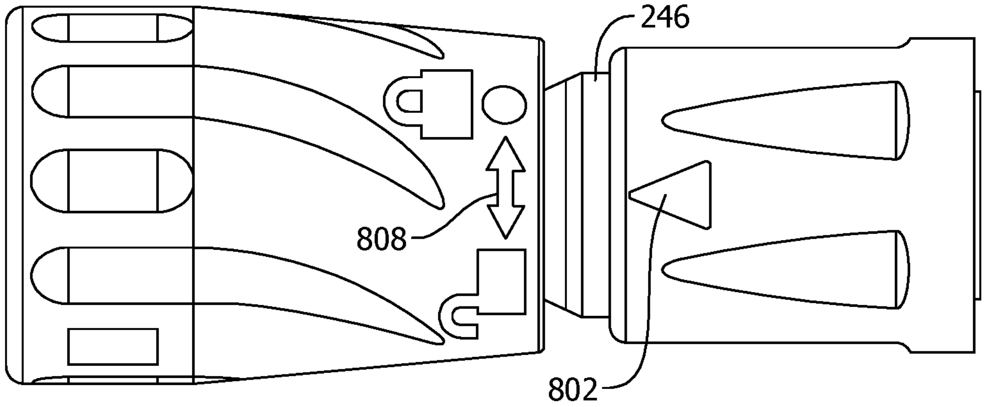

FIG. 8B shows connector insert 204 and housing 302 in the first locked configuration (i.e., with pin 252 engaging first locking detent 314). In this configuration, indicator line 246 is still visible. Further, arrow indicator 802 is generally aligned with a middle of transition indicator 808 in this configuration.

Figure 8C:
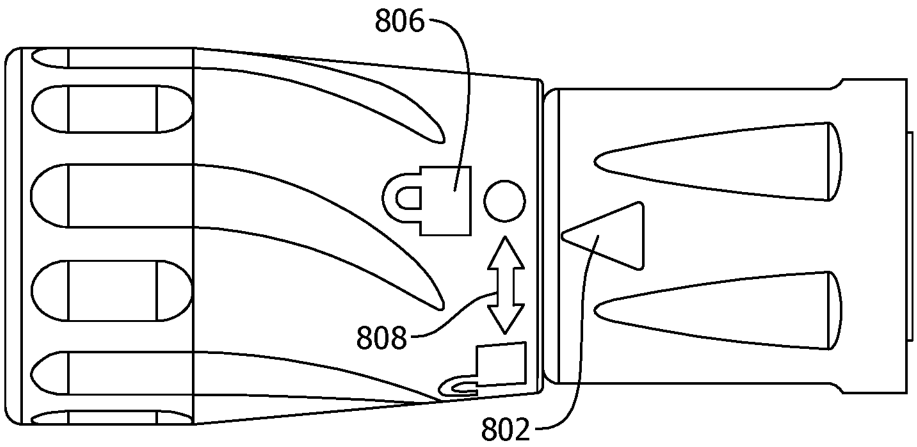

FIG. 8C shows connector insert 204 and housing 302 in a configuration between the first locked configuration and the second locked configuration (i.e., with pin 252 in groove 312 between first locking detent 314 and second locking detent 316). In this configuration, indicator line 246 is no longer visible. In addition, arrow indicator 802 is generally aligned with a second end of transition indicator 808 proximate lock indicator 806.

Figure 8D:
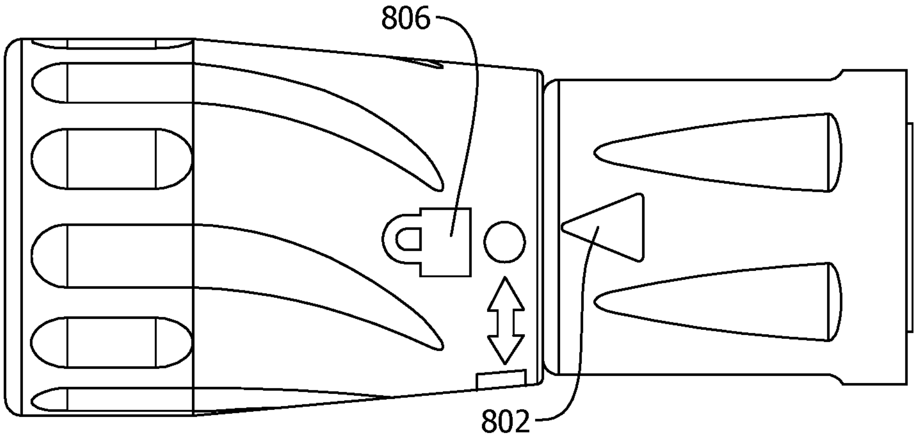

FIG. 8D shows connector insert 204 and housing 302 in the second locked configuration (i.e., with pin 252 engaging second locking detent 316). In this configuration, indicator line 246 is not visible, and arrow indicator 802 is generally aligned with lock indicator 806, demonstrating that connector insert 204 is fully engaged with connector receptacle 202.

The first and second locked configurations of connector system 200 provide advantages over at least some known connectors. For example, a user is able to confirm connector insert 204 is fully engaged with connector receptacle 202 by inserting connector insert 204 until the user detects (e.g., by tactile feedback, by observing indicator line 226, and by observing the various indicators on connector insert 204 and housing 302) that the first locked configuration is achieved, and then by further inserting connector insert 204 until the user detects (e.g., by tactile feedback, by observing indicator line 226, and by observing the various indicators on connector insert 204 and housing 302) that the second locked configuration is achieved.

Further, once connector system 200 is in the second locked configuration, if pin 252 inadvertently disengages from second locking detent 316 (e.g., due to a user manipulating and/or adjusting connector system 200), pin 252 will slide into first locking detect 314, instead of causing connector insert 204 to disengage from connector receptacle 202. Notably, connector system 200 is functional (i.e., provides an electrical and mechanical connection) in both the first and second locked configurations.

The embodiments described herein provide systems and methods for connections in a medical device system. A connector system includes a connector receptacle including first electrical contacts, a connector insert including second electrical contacts and at least one pin, and a locking member rotatably coupled to the connector receptacle. The locking member includes a housing and a guide member, the guide member including an annular body that defines at least one groove including a first locking detent and a second locking detent. The at least one pin is operable to traverse the at least one groove, engage the first locking detent in a first locked configuration, and engage the second locking detent in a second locked configuration when the connector insert is inserted into the connector receptacle.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A connector system for a medical device system, the connector system comprising:

a connector receptacle comprising first electrical contacts;

a connector insert comprising second electrical contacts and at least one pin; and a locking member rotatably coupled to the connector receptacle, the locking member comprising a housing and a guide member, the guide member comprising an annular body that defines at least one groove including a first locking detent and a second locking detent, the at least one pin operable to traverse the at least one groove, engage the first locking detent in a first locked configuration, and engage the second locking detent in a second locked configuration when the connector insert is inserted into the connector receptacle.

2. The connector system of claim 1, wherein the first electrical contacts are configured to be electrically coupled to the second electrical contacts in both the first locked configuration and the second locked configuration.

3. The connector system of claim 1, wherein the guide member further comprises a flexible finger configured to urge the at least one pin into the first and second locking detents.

4. The connector system of claim 1, wherein the connector receptacle further comprises at least one cam surface oriented to guide the at least one pin into the at least one groove.

5. The connector system of claim 1, wherein the connector insert comprises an indicator line that i) is visible from an exterior of the connector system when the connector system is in the first locked configuration and ii) is not visible from the exterior when the connector system is in the second locked configuration.

6. The connector system of claim 1, wherein the at least one pin comprises two pins on opposite sides of the connector insert, and wherein the annular body defines two corresponding grooves.

7. The connector system of claim 1, wherein the connector system comprises a driveline connector for a ventricular assist device.

8. A medical device system comprising:

an implantable medical device;

a controller; and a driveline coupling the implantable medical device to the controller, the driveline comprising a connector system comprising:

a connector receptacle comprising first electrical contacts;

a connector insert comprising second electrical contacts and at least one pin; and a locking member rotatably coupled to the connector receptacle, the locking member comprising a housing and a guide member, the guide member comprising an annular body that defines at least one groove including a first locking detent and a second locking detent, the at least one pin operable to traverse the at least one groove, engage the first locking detent in a first locked configuration, and engage the second locking detent in a second locked configuration when the connector insert is inserted into the connector receptacle.

9. The medical device system of claim 8, wherein the first electrical contacts are configured to be electrically coupled to the second electrical contacts in both the first locked configuration and the second locked configuration.

10. The medical device system of claim 8, wherein the guide member further comprises a flexible finger configured to urge the at least one pin into the first and second locking detents.

11. The medical device system of claim 8, wherein the connector receptacle further comprises at least one cam surface oriented to guide the at least one pin into the at least one groove.

12. The medical device system of claim 8, wherein the connector insert comprises an indicator line that i) is visible from an exterior of the connector system when the connector system is in the first locked configuration and ii) is not visible from the exterior when the connector system is in the second locked configuration.

13. The medical device system of claim 8, wherein the at least one pin comprises two pins on opposite sides of the connector insert, and wherein the annular body defines two corresponding grooves.

14. The medical device system of claim 8, wherein the implantable medical device comprises a ventricular assist device.

15. A method of assembling a connector system for use in a medical device system, the method comprising:

coupling a connector receptacle to an end of a first piece of a driveline, the connector receptacle including first electrical contacts;

coupling a connector insert to an end of a second piece of the driveline, the connector insert including second electrical contacts and at least one pin; and rotatably coupling a locking member to the connector receptacle, the locking member including a housing and a guide member, the guide member including an annular body that defines at least one groove including a first locking detent and a second locking detent, the at least one pin operable to traverse the at least one groove, engage the first locking detent in a first locked configuration, and engage the second locking detent in a second locked configuration when the connector insert is inserted into the connector receptacle.

16. The method of claim 15, wherein the first electrical contacts are configured to be electrically coupled to the second electrical contacts in both the first locked configuration and the second locked configuration.

17. The method of claim 15, wherein the guide member further includes a flexible finger configured to urge the at least one pin into the first and second locking detents.

18. The method of claim 15, wherein the connector receptacle further includes at least one cam surface oriented to guide the at least one pin into the at least one groove.

19. The method of claim 15, wherein the connector insert includes an indicator line that i) is visible from an exterior of the connector system when the connector system is in the first locked configuration and ii) is not visible from the exterior when the connector system is in the second locked configuration.

20. The method of claim 15, wherein the at least one pin includes two pins on opposite sides of the connector insert, and wherein the annular body defines two corresponding grooves.

* * * * *